United States Patent
Schomacker

(10) Patent No.: US 11,439,463 B2
(45) Date of Patent: Sep. 13, 2022

(54) LASER SYSTEM WITH CONTROLLED FIRING OF COOLING AGENT AND LASER BASED ON APPLICATOR POSITION

(71) Applicant: Candela Corporation, Wayland, MA (US)

(72) Inventor: Kevin Schomacker, Maynard, MA (US)

(73) Assignee: CANDELA CORPORATION, Marlborough, MA (US)

( * ) Notice: Subject to any disclaimer, the term of this patent is extended or adjusted under 35 U.S.C. 154(b) by 342 days.

(21) Appl. No.: 16/395,291

(22) Filed: Apr. 26, 2019

(65) Prior Publication Data
US 2020/0337771 A1    Oct. 29, 2020

(51) Int. Cl.
*A61B 18/22* (2006.01)
*A61B 18/20* (2006.01)
*A61B 18/00* (2006.01)

(52) U.S. Cl.
CPC ............ *A61B 18/22* (2013.01); *A61B 18/203* (2013.01); *A61B 2018/00017* (2013.01); *A61B 2018/00029* (2013.01); *A61B 2018/0047* (2013.01); *A61B 2018/00476* (2013.01); *A61B 2018/205545* (2017.05)

(58) Field of Classification Search
CPC .... A61B 2018/203; A61B 2018/00476; A61B 2018/00029; A61B 2018/0047; A61B 2018/00017; A61B 2018/205545
See application file for complete search history.

(56) References Cited

U.S. PATENT DOCUMENTS

| | | |
|---|---|---|
| 6,171,301 B1 | 1/2001 | Nelson et al. |
| 6,758,845 B1 | 7/2004 | Weckwerth et al. |
| 11,097,124 B2 | 8/2021 | Kim et al. |

(Continued)

FOREIGN PATENT DOCUMENTS

| | | |
|---|---|---|
| KR | 100864803 B1 | 10/2008 |
| WO | 2013019785 A1 | 2/2013 |

OTHER PUBLICATIONS

International Search Report & Written Opinion in PCT/US2020/028193 dated Jul. 31, 2020.

(Continued)

*Primary Examiner* — Lynsey C Eiseman
*Assistant Examiner* — Amanda L Steinberg
(74) *Attorney, Agent, or Firm* — Manelli Selter PLLC; Edward Stemberger

(57) ABSTRACT

A laser system includes a base unit having a power source. A hand-held applicator is connected with the base unit configured to engage biological tissue for treatment. Position detection structure is associated with the applicator for determining a position of the applicator relative to the engaged biological tissue. A laser source generates a laser beam. A cooling system provides a cooling agent to the biological tissue during treatment. A processor circuit is connected with the position detection structure, the laser source and the cooling system. Based on data received from the position detection structure, the processor circuit triggers application of the cooling agent to the treated biological tissue, or triggers application of the cooling agent to the treated biological tissue, followed by a time delay, and then triggers the laser source.

17 Claims, 8 Drawing Sheets

(56) References Cited

U.S. PATENT DOCUMENTS

| | | | |
|---|---|---|---|
| 2001/0009997 A1 | 7/2001 | Pope et al. | |
| 2007/0083190 A1 | 4/2007 | Domankevitz | |
| 2007/0265605 A1* | 11/2007 | Vaynberg | A61C 17/0202 |
| | | | 606/13 |
| 2007/0270785 A1 | 11/2007 | Jones et al. | |
| 2012/0226268 A1* | 9/2012 | Liu | A61N 5/0613 |
| | | | 606/9 |
| 2012/0283711 A1 | 11/2012 | Liu et al. | |
| 2013/0150841 A1* | 6/2013 | Schomacker | A61B 18/203 |
| | | | 606/13 |
| 2014/0257254 A1* | 9/2014 | Boutoussov | A61B 18/203 |
| | | | 606/3 |
| 2015/0258347 A1 | 9/2015 | Neev | |
| 2016/0305795 A1* | 10/2016 | Eisenbeis | G01D 7/007 |

OTHER PUBLICATIONS

Partial International Search Report in PCT/US2020/028193 dated Jun. 5, 2020.

* cited by examiner

LASER SYSTEM WITH CONTROLLED FIRING OF COOLING AGENT AND LASER BASED ON APPLICATOR POSITION

FIELD

The embodiment relates to a laser system for biological tissue treatment such as hair removal treatment and laser skin treatment and, more particularly, to a laser system employing controlled firing of a cooling agent and laser based on a position of an applicator or hand-piece during the tissue treatment.

BACKGROUND

A conventional laser apparatus such as the Ellipse® FRAX 1550 fractional non-ablating laser includes a hand-piece having a magnetic motion roller sensor that measures speed of movement of the roller across the skin surface and indicates this speed to the operator. The apparatus provides cooling air to continuously cool the skin being treated. A foot pedal is provided to activate the laser.

Although this conventional laser apparatus works well for it intended purpose, there is a need to provide a laser system having a dynamic cooling device (DCD), and a hand-piece applicator, with the system being constructed and arranged to control the firing of the DCD and the laser based on a position of the applicator relative to the tissue being treated.

SUMMARY

An objective of the embodiment is to fulfill the need referred to above. In accordance with the principles of an embodiment, this objective is achieved by a laser system including a base unit having a power source. A hand-held applicator is connected with the base unit and is constructed and arranged to engage biological tissue for treatment. Position detection structure is associated with the applicator and is constructed and arranged to determine a position of the applicator relative to the engaged biological tissue. A laser source is constructed and arranged to generate laser beam. A cooling system is constructed and arranged to provide a source of cooling agent to the biological tissue during treatment. A processor circuit is connected with the position detection structure, the laser source, and the cooling system. Based on data received from the position detection structure, the processor circuit is constructed and arranged to trigger application of the cooling agent to the treated biological tissue, or to trigger application of the cooling agent to the treated biological tissue, followed by a time delay, and then to trigger the laser source.

In accordance with another aspect of an embodiment, a hand-held applicator for treating biological tissue includes a body constructed and arranged to connect with a laser source. A magnetic roller is provided at a distal end of the body. A magnetic field sensor is associated with the magnet roller and is constructed and arranged to detect phase changes as the magnetic roller rotates. A valve is constructed and arranged generally with a nozzle to provide a source of cooling agent to the biological tissue during treatment. A trigger circuit is connected with the magnetic field sensor and the valve. Based on a number of phase changes detected by the magnetic field sensor as the magnetic roller rotates, the trigger circuit is constructed and arranged to trigger the valve to apply the cooling agent to the treated biological tissue.

In accordance with yet another aspect of an embodiment, a method treats biological tissue with a laser system. The laser system includes a hand-held applicator constructed and arranged to engage biological tissue for treatment; position detection structure associated with the applicator constructed and arranged to determine a position of the applicator relative to the engaged biological tissue; a laser source constructed and arranged to generate laser beam; a cooling system constructed and arranged to provide a cooling agent to the biological tissue during treatment; and a processor circuit connected with the position detection structure, the laser source and the cooling system. The method includes engaging the biological tissue with the applicator; moving the applicator relative to the engaged biological tissue; determining, with the position detection structure, a position of the applicator relative to the engaged biological tissue; and based on the position of the applicator relative to the engaged biological tissue, triggering the cooling system with the processor circuit to provide the cooling agent to the biological tissue during treatment. After a time delay, the processor circuit triggers the laser source.

Other objectives, features and characteristics of the present embodiment, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF THE EXEMPLARY EMBODIMENTS

Figure 1:
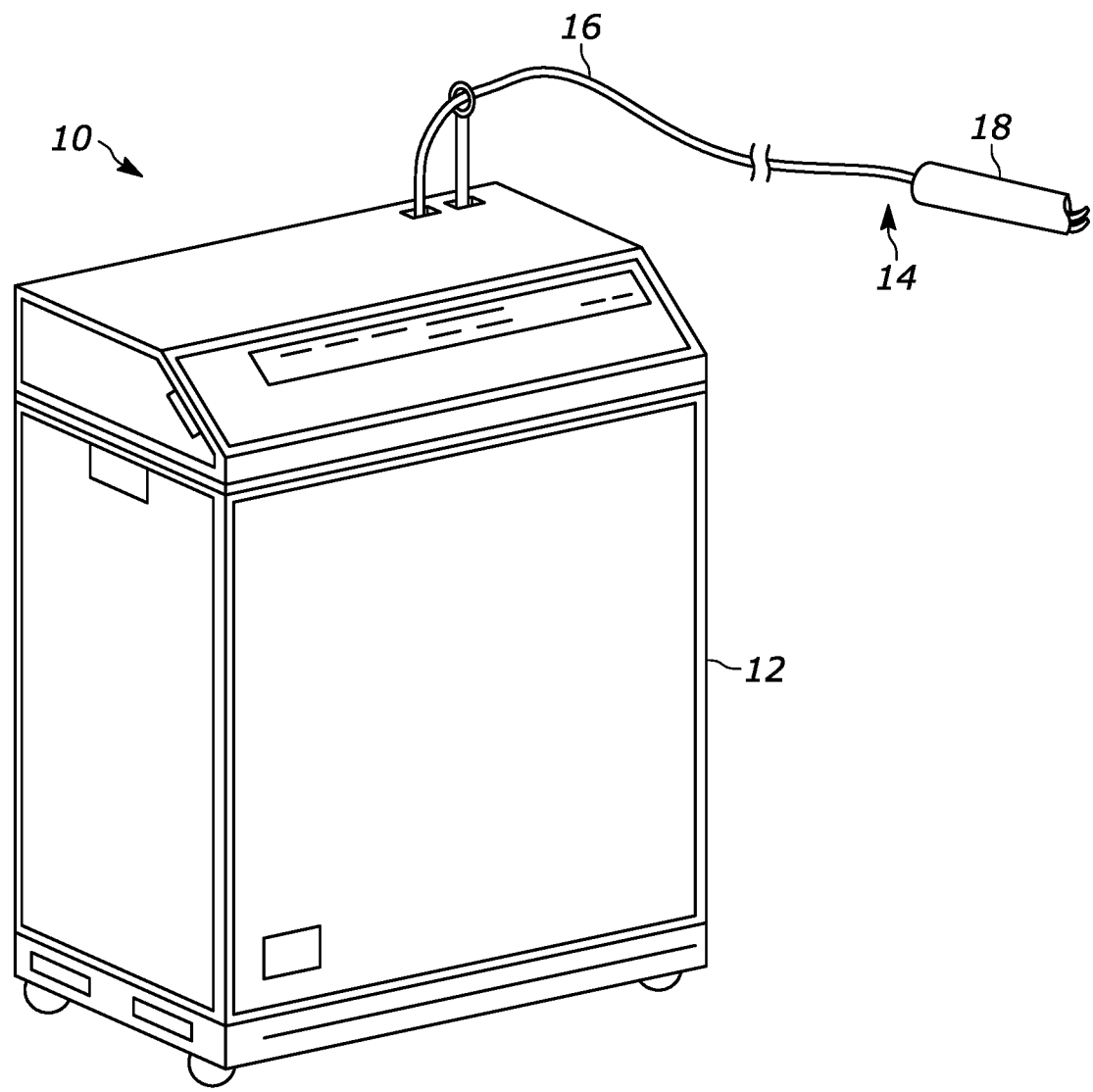
FIG. 1 is a perspective view of a laser system provided in accordance with an embodiment.

With reference to FIG. 1, an embodiment of a laser system is shown, generally indicated at 10, for treating biological tissue. The system 10 can be used to non-invasively deliver radiation to target biological tissue such as the skin or hair. The system 10 includes a base unit 12 and a delivery system, generally indicated at 14. In one embodiment, laser radiation provided by the energy source 12 is directed via the delivery system 14 to the target tissue. In the illustrated embodiment, the delivery system 14 includes an umbilical cable 16 and an applicator 18. The applicator 18 can be a handheld device, such as a handpiece, which can be held or manipulated by a user to irradiate the target tissue.

Figure 2:
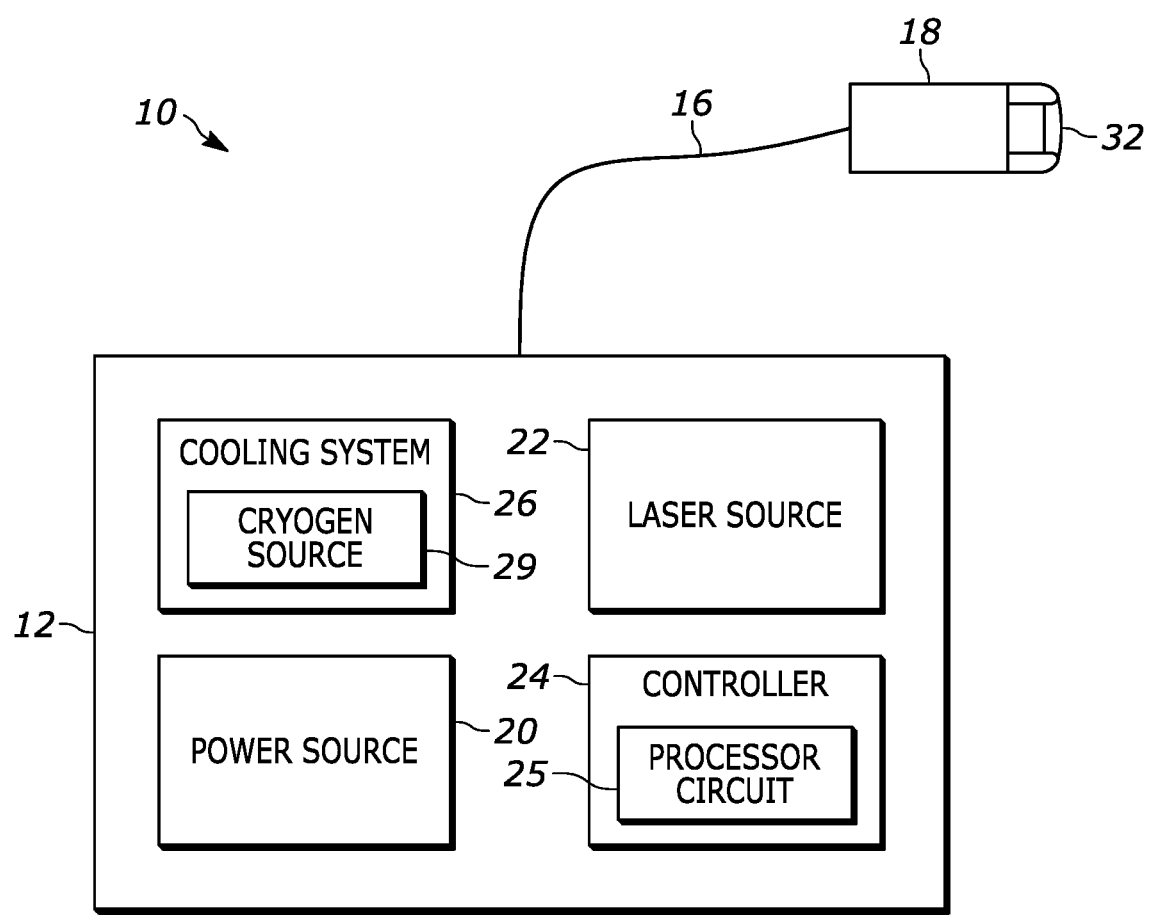
FIG. 2 is schematic illustration of the laser system of FIG. 1.

As shown in FIG. 2, the base unit 12 is coupled to the umbilical cable 16, which is connected to a delivery module 14. The base unit 12 includes a power source 20 that supplies power to various system components, including a laser source 22 housed in the base unit 12 for emitting a laser beam L (FIG. 3) through the umbilical cable 16 and applicator 18 to the target tissue. A foot pedal (not shown) or finger switch on the applicator 18 can be employed to arm the laser source 22. The base unit 12 also includes a controller 24 coupled with the laser source 22 and which can be coupled to a user interface. The controller 24 includes a processor circuit 25.

Figure 3:
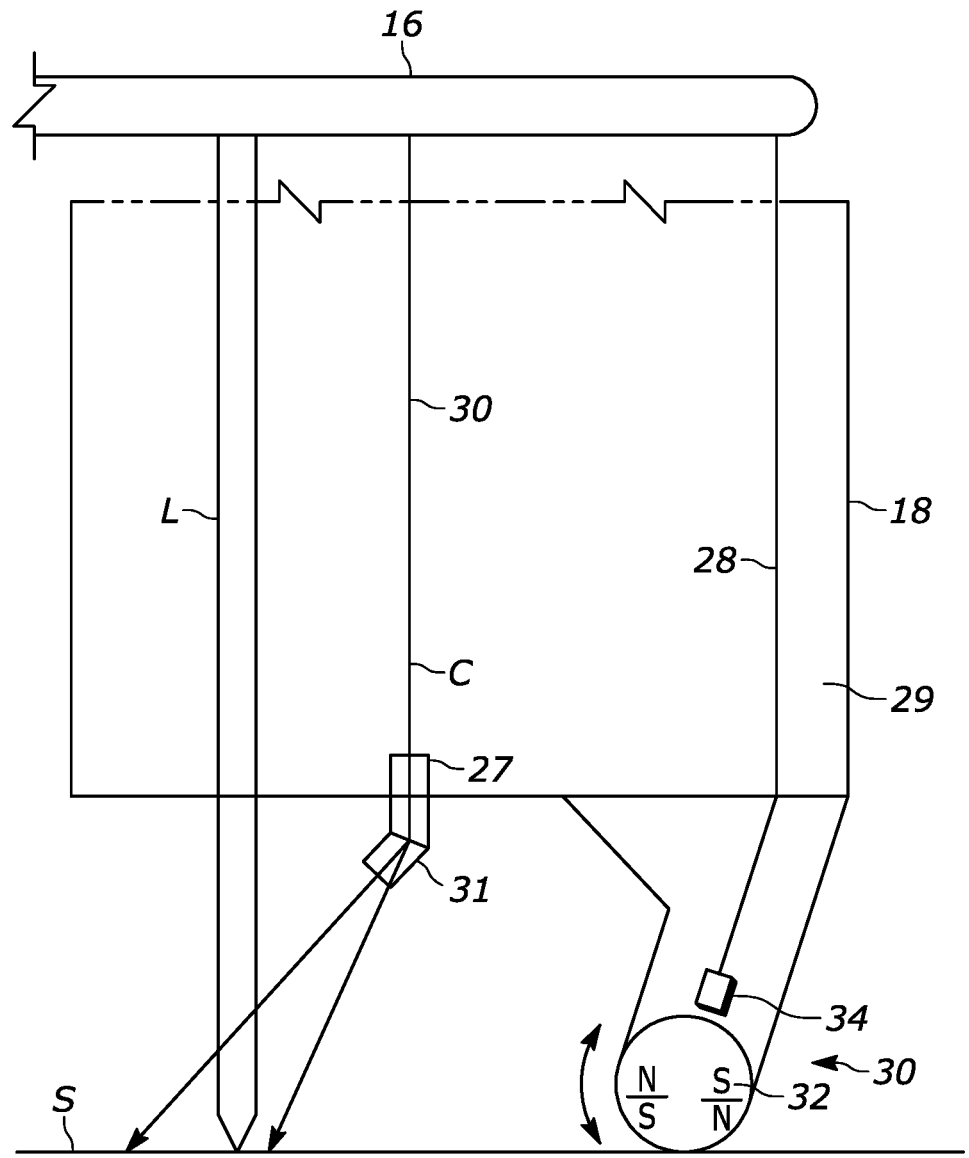
FIG. 3 is a partial schematic side view of the applicator of the laser system of FIG. 2.
Figure 4:
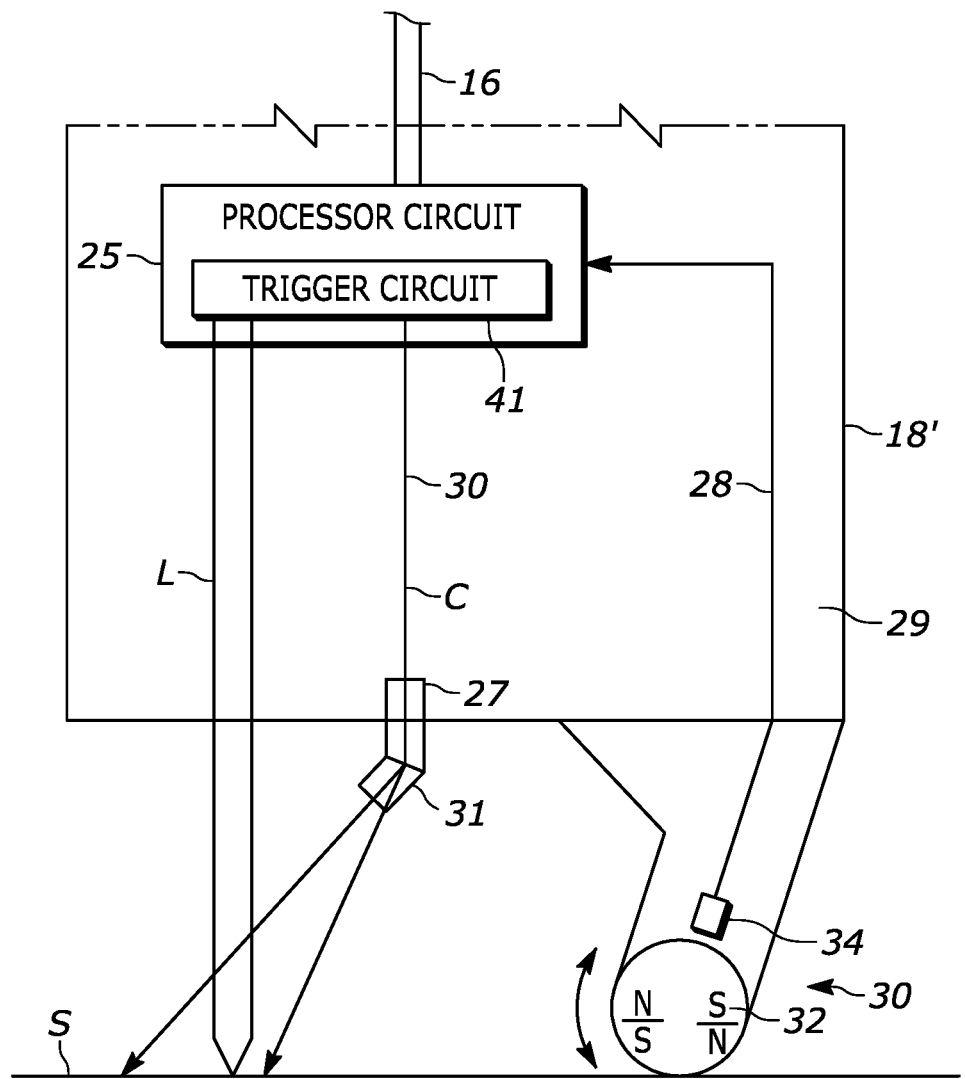
FIG. 4 is a partial schematic side view of another embodiment of the applicator of the laser system.

The base unit 12 includes a cooling system 26 for minimizing unwanted thermal injury to tissue. The cooling system 26 includes a dynamic cooling device (DCD) that prevents damage to the epidermis during laser hair removal or skin treatments. The cooling system contains 26 cooling agent such as a source of cryogen gas C in the base unit 12. With reference to FIG. 3, a DCD spray valve 27 at the applicator 18 is connected with cryogen gas source 29. The DCD works by spraying, via the valve 27 (with nozzle 31), the outer layers of the skin with a cryogen gas C. The cryogen gas can be applied on the skin for about 50 ms directly before and/or after each laser pulse. The DCD works by cooling the top layer of the skin without disturbing the layers beneath. This allows the targeted hair follicles, veins, and other layers of the skin to remain at normal or near normal temperature. With reference to FIG. 3, the umbilical cable 16 can house at least one of an electrical communication line 28 and a coolant line connected to valve 27. With reference to FIG. 4, alternatively, the controller 24 and/or processor circuit 25 can be housed in the applicator 18' instead of the base unit 12.

Figure 5:
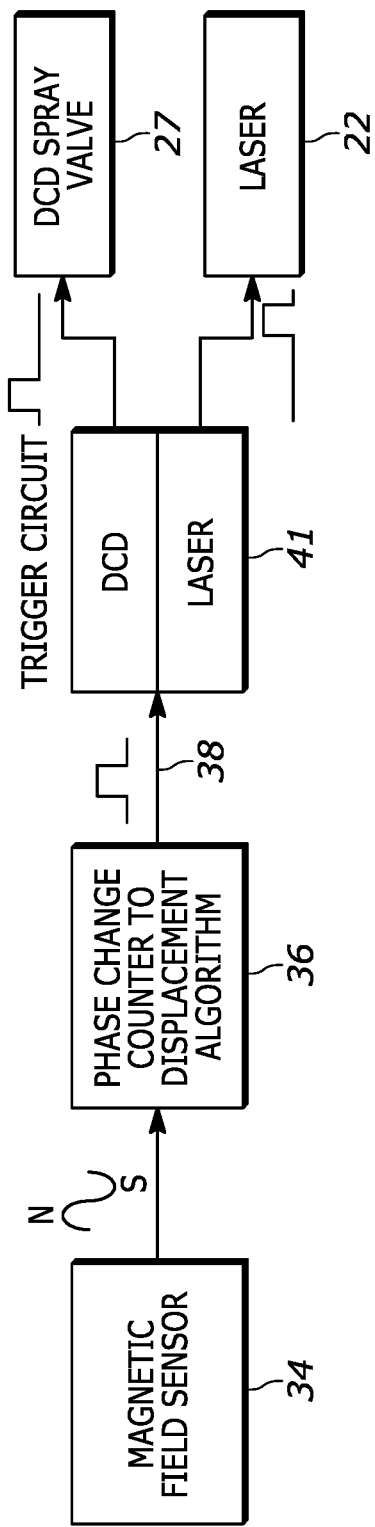
FIG. 5 is a schematic illustration for triggering of the DCD spray valve and/or laser source based on signals detected by the magnetic field sensor of an embodiment.

As shown in FIGS. 3 and 4, the applicator 18, 18' includes a body 29 and position detection structure, generally indicated at 30, is provided at a distal end of the body 29. In the embodiment, the position detection structure 30 includes a magnetic roller 32 and a magnetic field sensor 34, such as a Hall-effect sensor. As shown, north and south poles of the magnetic roller 32 oppose each other. The strength of the magnetic field created by the magnetic roller 32 is detected by the stationary magnetic field sensor 34 disposed generally adjacent to the magnetic roller 32. As the magnetic roller 32 rotates along the skin surface S, the magnetic field sensor 34 detects phase changes caused by the rotating magnetic roller 32 (see step 40 in FIG. 10). With reference to FIG. 5, an algorithm 36 is executed by the processor circuit 25 converting phase changes counted by the magnetic field sensor 34 to a displacement value of the magnetic roller 32 in accordance with the following formula:

$$\text{Displacement } (d) = \\ \text{number of phase changes } (N_{pc}) \times \frac{\text{roller circumference } (\pi D)}{2}$$

$$d = N_{pc} \times \frac{\pi D}{2}$$

Figure 6:
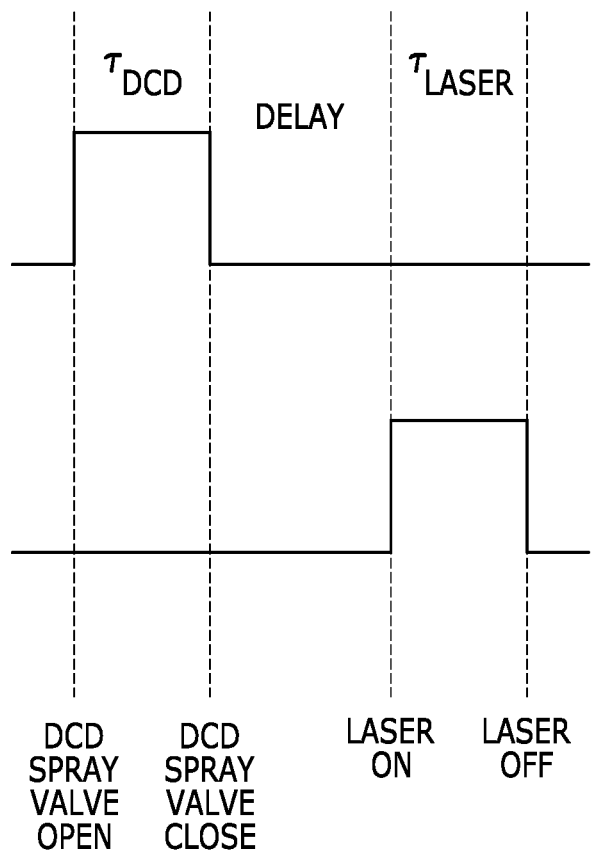
FIG. 6 shows trigger signals for triggering the DCD spray valve and laser source in accordance with an embodiment.
Figure 7:
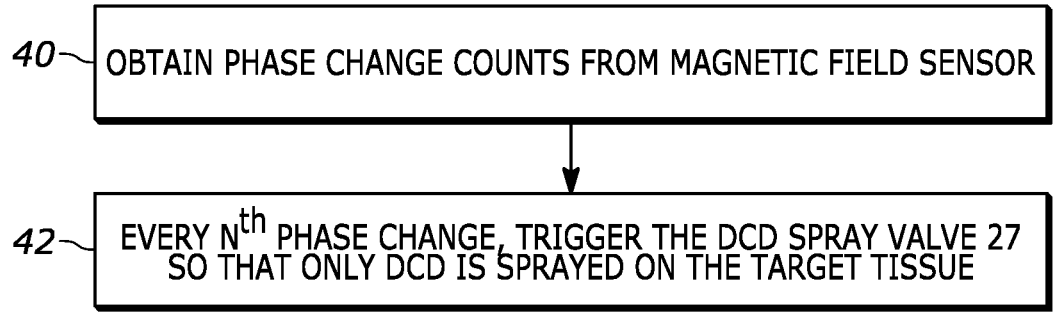
FIG. 7 is a flow chart of steps for performing a method of an embodiment.
Figure 8:
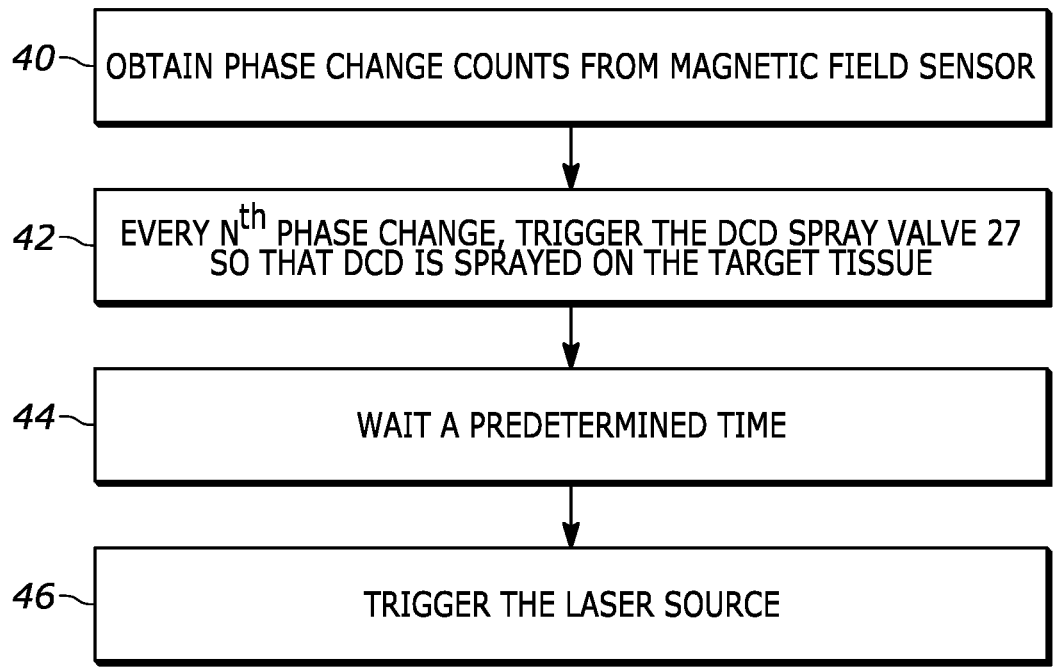
FIG. 8 is a flow chart of steps for performing a method of another embodiment.
Figure 9:
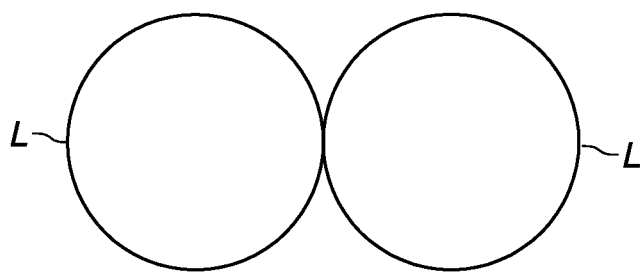
FIG. 9 is a plan view of successive circular cross-section laser beams delivered to the target tissue with no overlap.
Figure 11:
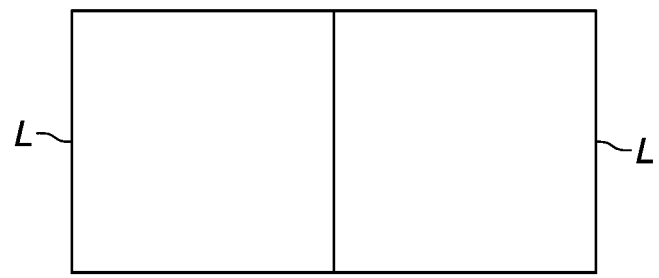
FIG. 11 is a plan view of successive square cross-section laser beams delivered to the target tissue with no overlap.
Figure 12:
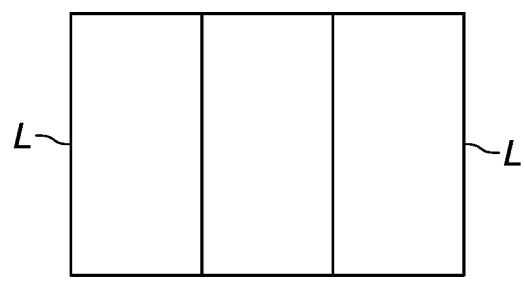
FIG. 12 is a plan view of successive square cross-section laser beams delivered to the target tissue with overlap.

The displacement signal 38 is received by a trigger circuit 41 which can be considered to be part of the processor circuit 25. With reference to FIG. 6, the DCD and laser triggering sequence will be appreciated. From an initial position of the hand-piece on the target tissue, every $N^{th}$ phase change can trigger (open), via the trigger circuit 41, the DCD spray valve 27 so that only the cooling agent C is sprayed via nozzle 31 on the target tissue (step 42 in FIG. 7), or the trigger circuit 41 can trigger the DCD spray valve 27 so that the cooling agent C is sprayed via nozzle 31 on the target tissue (step 42 in FIG. 8), followed by a predetermined time delay (step 44 in FIG. 8), then can trigger the laser source 22 (step 46 in FIG. 8). For perfect beam L delivery to the target tissue with no overlap (FIGS. 9, 11), displacement d is set to equal the beam width as measured in the direction of displacement. For beam L overlap (FIGS. 10, 12), displacement d is set to a fraction of the beam width (e.g., 80%).

Resolution of the magnetic field sensor 34 can be improved by employing multiple Hall-effect sensors defining the magnetic field sensor 34, employing multiple magnets in the magnetic roller 32 or a combination of both of these. Alternatively, other embodiments of the position detection structure 30 can be employed. For example, the position of the roller 32 can be obtained with a rotary encoder (not shown) that measures direct linear motion. The circumference of the roller 32 is related to the pulse per revolution (PPR) of the encoder. If the roller rotated a full turn (360 angular degrees), the distance traveled would be equal to the circumference of the roller. A stabilizing roller (not shown) can be provided adjacent to the magnetic roller 32 on the opposite side of the cryogen spray for increased stabilization of the applicator 18 when rolling upon the target tissue. The stabilization roller helps to ensure that the applicator is held perpendicular to the skin surface. The position sensor works best when the displacement of the applicator is small relative to the time it takes to deliver the cryogen spray or cryogen spray and laser. A typical time is 10 to 100 ms, which correlates to a maximum 3.6 mm displacement if traveling at a speed of 36 mm/s (two 18 mm beam widths per second). The displacement during a 3 ms laser pulse is small, about 0.1 mm for a speed of 36 mm/s.

Figure 10:
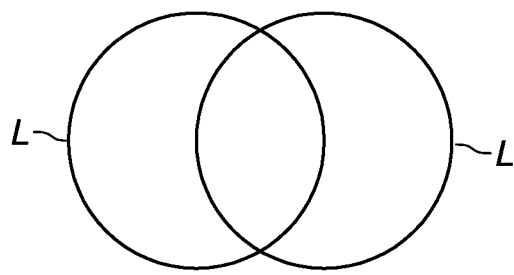
FIG. 10 is a plan view of successive circular cross-section laser beams delivered to the target tissue with overlap.

The cross-section of the laser beam L on the tissue surface can be circular, rectangular, square or hexagonal in shape. Rectangular and square beams are the preferred choice for cases where 100% coverage is needed without overlap. A prism can be provided to shape the laser beam L. Alternatively, optical fibers having round or rectangular cores can be used. Or alternately, diffractive optic elements can be used to convert a round beam to a rectangular beam. Since generally large areas of skin or hair are being treated, it is preferable that successive laser beams be directly adjacent (e.g., touching, FIG. 9) or, for better treatment coverage, the successive laser beams L can overlap (FIG. 10).

The system 10 can be employed for multiple applications such as hair removal; vascular lesion treatments such as treating port wine stains and spider veins; and reduction of pigment and skin rejuvenation such as treating rosacea, acne, pigmented lesions, and sun damaged skin. For use in hair removal, the laser source 22 is preferably one of a 755 nm Alexandrite laser, a semiconductor diode laser operated around 800 nm, preferably at 805 nm or 810 nm, and a 1064 nm Nd:YAG laser preferably employed to a depth of about 4 mm. For use in vascular lesion and pigment treatment, the laser source 22 is preferably one of a 532 nm KTP laser, a 1064 nm Nd:YAG laser, a dye laser operated at 585 nm or 595 nm, or a 755 Alexandrite laser. For vascular lesions, the treatment is preferably at a depth of about 1 mm and for pigment and skin rejuvenation, the treatment is preferably at a depth of about 0.1-0.2 mm. The system 10 works well for treating a significant area of tissue, such as vascular treatments on most of an entire face, or hair removal treatments on legs or a man's back.

The operations and algorithms described herein can be implemented as executable code within the processor circuit 25 as described, or stored on a standalone computer or machine readable non-transitory tangible storage medium that are completed based on execution of the code by a processor circuit implemented using one or more integrated circuits. Example implementations of the disclosed circuits include hardware logic that is implemented in a logic array such as a programmable logic array (PLA), a field programmable gate array (FPGA), or by mask programming of integrated circuits such as an application-specific integrated circuit (ASIC). Any of these circuits also can be implemented using a software-based executable resource that is executed by a corresponding internal processor circuit such as a micro-processor circuit (not shown) and implemented using one or more integrated circuits, where execution of executable code stored in an internal memory circuit causes the integrated circuit(s) implementing the processor circuit to store application state variables in processor memory, creating an executable application resource (e.g., an application instance) that performs the operations of the circuit as described herein. Hence, use of the term "circuit" in this specification refers to both a hardware-based circuit implemented using one or more integrated circuits and that includes logic for performing the described operations, or a software-based circuit that includes a processor circuit 25 (implemented using one or more integrated circuits), the processor circuit including a reserved portion of processor memory for storage of application state data and application variables that are modified by execution of the executable code by a processor circuit. The memory circuit can be implemented, for example, using a non-volatile memory such as a programmable read only memory (PROM) or an EPROM, and/or a volatile memory such as a DRAM, etc.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A laser system comprising:
   a base unit having a power source,
   a hand-held applicator connected with the base unit and constructed and arranged to engage biological tissue for treatment,
   position detection structure associated with the applicator constructed and arranged to determine displacement of the applicator as the applicator is moved along the engaged biological tissue,
   a laser source constructed and arranged to generate laser beam,
   a cooling system constructed and arranged to provide a source of cooling agent to the biological tissue during treatment, and
   a processor circuit connected with the position detection structure, the laser source, and the cooling system,
   wherein, based on the displacement received from the position detection structure and on a width of the laser beam as measured in the direction of displacement of the applicator, the processor circuit is constructed and arranged to trigger application of the cooling agent to the treated biological tissue, followed by a time delay, and then to trigger the laser source.

2. The system of claim 1, wherein the laser source, cooling system and processing circuit are housed in the base unit.

3. The system of claim 1, wherein the laser source and cooling system are housed in the base unit and wherein the processor circuit is housed in the applicator.

4. The system of claim 1, wherein the position detection structure comprises a magnetic roller and a magnetic field sensor associated with the magnetic roller and constructed and arranged to detect phase changes as the magnetic roller rotates.

5. The system of claim 4, wherein the magnetic field sensor comprises at least one Hall-effect sensor.

6. The system of claim 5, wherein the processor circuit is constructed and arranged to convert phase changes counted by the Hall-effect sensor to a displacement value of the magnetic roller.

7. The system of claim 6, wherein the processor circuit includes a trigger circuit constructed and arranged to cause the trigger of the cooling agent and the laser source based on the displacement of the magnetic roller.

8. The system of claim 7, wherein the applicator includes a spray valve constructed and arranged to be triggered between open and closed positions by the trigger circuit to deliver the cooling agent from the cooling system.

9. The system of claim 6, wherein the processor circuit is constructed and arranged to execute the following formula:

$$\text{Displacement }(d) = \text{number of phase changes }(N_{pc}) \times \frac{\text{roller circumference }(\pi D)}{2}$$

$$d = N_{pc} \times \frac{\pi D}{2}.$$

where D is the diameter of the magnetic roller.

10. The system of claim 1, wherein the laser source is a 755 nm Alexandrite laser; a semiconductor diode laser operated around 800 nm; a 1064 nm Nd:YAG laser; a 532 nm KTP laser; or a dye laser operated at 585 nm or 595 nm.

11. The system of claim 1, wherein the laser source is constructed and arranged to generate successive laser beams that are adjacent and touching with no overlap, with the displacement being equal to the laser beam width.

12. The system of claim 1, wherein the laser source is constructed and arranged to generate successive laser beams that are adjacent and overlap, with the displacement being 80% of the laser beam width.

13. A laser system comprising:
   a base unit having a power source,
   a hand-held applicator connected with the base unit and constructed and arranged to engage biological tissue for treatment,
   position detection structure associated with the applicator constructed and arranged to determine a distance traveled of the applicator as the applicator is moved along the engaged biological tissue,
   a cooling system constructed and arranged to provide a source of cooling agent to the biological tissue during treatment, and
   a processor circuit connected with the position detection structure and the cooling system,
   wherein, based on the distance traveled of the applicator as received from the position detection structure, the processor circuit is constructed and arranged to trigger application of the cooling agent to the treated biological tissue.

14. The system of claim 13, wherein the hand-held applicator includes a spray valve constructed and arranged to supply the cooling agent once the spray valve is triggered by the processor circuit.

15. The system of claim 14, wherein the processor circuit is constructed and arranged to trigger the spray valve to supply the cooling agent for 10 to 100 ms.

16. The system of claim 15, wherein the cooling agent is a cryogen gas.

17. The system of claim 13, wherein the position detection structure comprises a magnetic roller and a magnetic field sensor associated with the magnetic roller and constructed and arranged to detect phase changes as the magnetic roller rotates.

* * * * *